United States Patent
Broadbent et al.

(10) Patent No.: US 7,259,566 B2
(45) Date of Patent: Aug. 21, 2007

(54) MICRO SENSOR SYSTEM FOR LIQUID CONDUCTIVITY, TEMPERATURE AND DEPTH

(75) Inventors: Heather A. Broadbent, St. Petersburg, FL (US); David P. Fries, St. Petersburg, FL (US); George T. Steimle, St. Petersburg, FL (US); Stanislav Ivanov, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/358,430

(22) Filed: Feb. 21, 2006

(65) Prior Publication Data

US 2007/0018652 A1 Jan. 25, 2007

Related U.S. Application Data

(60) Provisional application No. 60/593,874, filed on Feb. 21, 2005.

(51) Int. Cl.
*G01N 27/02* (2006.01)

(52) U.S. Cl. ............................... 324/446; 324/693

(58) Field of Classification Search ............... 324/446, 324/693
See application file for complete search history.

(56) References Cited

U.S. PATENT DOCUMENTS

| 4,777,819 | A | 10/1988 | Hoyt et al. |
| 5,209,112 | A | 5/1993 | McCoy et al. |
| 5,767,682 | A | 6/1998 | Sekimoto et al. |
| 6,577,134 | B2 | 6/2003 | Farruggia et al. |
| 6,958,693 | B2 * | 10/2005 | Rothgeb et al. ........ 340/539.22 |
| 7,082,834 | B2 * | 8/2006 | Petrova et al. ................. 73/708 |
| 2002/0167322 | A1 * | 11/2002 | He et al. ..................... 324/441 |
| 2004/0015618 | A1 | 1/2004 | Risi et al. |
| 2004/0238357 | A1 * | 12/2004 | Bhullar et al. .............. 204/400 |
| 2006/0147700 | A1 * | 7/2006 | Papakostas et al. ......... 428/323 |

* cited by examiner

*Primary Examiner*—Walter Benson
(74) *Attorney, Agent, or Firm*—Molly L. Sauter; Smith & Hopen, P.A.

(57) ABSTRACT

In accordance with the present invention is a miniature planar oceanographic conductivity, temperature pressure (CTD) system based on a thin film material fabricated on a Liquid Crystalline Polymer (LCP). The micro-CTD system in accordance with the present invention analyzes water for salinity by measuring conductivity, temperature and depth.

13 Claims, 5 Drawing Sheets

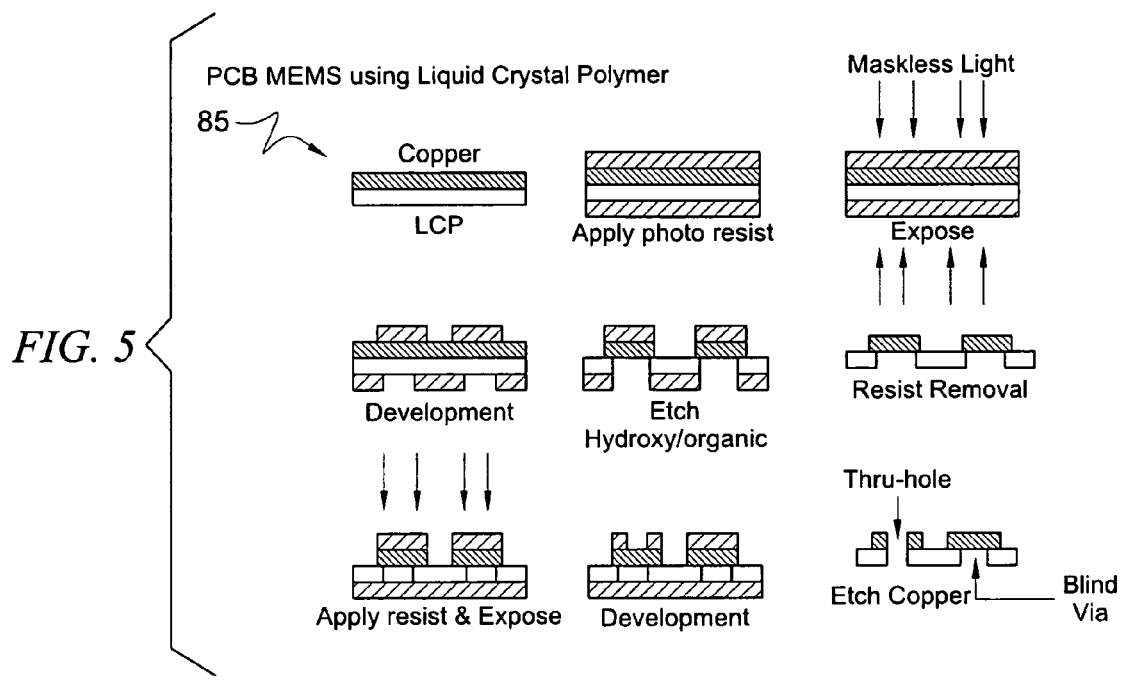
*FIG. 5*
*FIG. 6A*
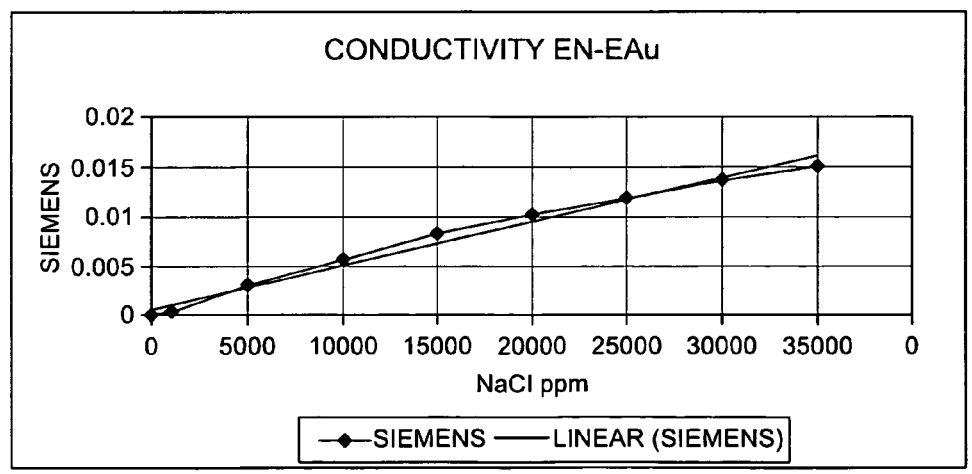

MICRO SENSOR SYSTEM FOR LIQUID CONDUCTIVITY, TEMPERATURE AND DEPTH

CROSS REFERENCE TO RELATED APPLICATIONS

This application claims priority to U.S. Provisional Patent Application No. 60/593,874 entitled: "Micro-CTD System," filed by the same inventors on Feb. 21, 2005.

GOVERNMENT SUPPORT

This invention was developed under support from the Office of Naval Research; accordingly the U.S. government has certain rights in the invention.

BACKGROUND OF INVENTION

Salinity is an important and fundamental chemical property of seawater that directly affects biological and physical processes of the oceans and coastal waters. Available instrumentation for measuring salinity is severely limited by accuracy, power, long-term stability, and high cost. Commonly, salinity measurements are determined by using a CTD instrument, which simultaneously measures conductivity, temperature and depth of the water. For a water sample of known temperature and pressure the salinity can be determined by measuring the conductivity of the sample. CTD data provides critical information to all fields of marine science research including chemical, biological, physical and geological.

There are various CTD systems currently known in the art. CTD systems constructed utilizing large scale electrodes are currently available. The size of these CTD systems severely limits their flexibility and adaptability to various applications. Inductive style CTD systems are also known in the art. These inductive systems are limited by their large physical size to sensed volume and long flushing lengths. These inductive CTD systems are based on embedded ceramic technology.

Accordingly, what is needed in the art is a CTD system that allows for mass production and miniaturization of a CTD would be beneficial to the oceanographic community and water quality measurers.

SUMMARY OF INVENTION

In accordance with the present invention is a miniature oceanographic CTD system based on a thin film material, Liquid Crystalline Polymer (LCP) or any other standard printed circuit board substrate material. The micro-CTD system in accordance with the present invention analyzes water for salinity by measuring conductivity, temperature and depth.

In a particular embodiment, the miniature CTD system is manufactured utilizing a PCBMEMS fabrication technique. In an additional embodiment, the miniature CTD system is manufactured utilizing a Laminate MEMS fabrication technique.

In accordance with the present invention is provided an apparatus for measuring conductivity, temperature and depth of a liquid, the apparatus including a substantially planar thin-film conductivity microsensor for measuring the conductivity of the liquid, a substantially planar thin-film resistive temperature microsensor for measuring the temperature of the liquid and a discrete pressure microsensor for measuring the pressure of the liquid.

In a specific embodiment, the conductivity microsensor is a four electrode conductivity sensor further including four concentric annular electrodes fixed in relative position to each other. These electrodes are preferably fabricated on a liquid crystalline polymer substrate, but other substrates commonly employed in the art are within the scope of the invention.

Various metal layer configurations are envisioned for the conductivity sensor electrodes, including but not limited to electroless nickel/electroless gold, electroless nickel/electrolytic gold and electroless nickel/electrolytic gold/platinum black.

In addition to the electrodes, the conductivity microsensor further includes appropriate supply circuitry and output circuitry to effecting the measuring of the conductivity of the liquid.

In an additional embodiment, the substantially planar thin-film resistive temperature microsensor further is a thin-film metallic circuit exhibiting a linear change in resistance with a change in the temperature of the liquid. In a specific embodiment, the resistive temperature microsensor consists of two parallel metallic traces having 90° angles and meeting at a center point. These metal traces may be fabricated on a copper-clad liquid crystalline polymer substrate or other substrates commonly employed in the art.

The present invention also includes a discrete pressure microsensor to measure the pressure of the liquid. In a particular embodiment, this pressure microsensor is a piezoresistive pressure sensor.

In order to communicate the collected measurements from the microsensors, the present invention includes a data-acquisition and processing system connected to receive measurement signals from the conductivity microsensor, the temperature microsensor and the pressure microsensor. Additionally, the collected measurements may be transmitted to a user through the use of embedded wireless functionality or the apparatus may be controlled from a remote location through wireless technology.

To protect the measurement apparatus from corrosion, the circuitry may be encased in a substantially watertight casing with only the necessary sensor elements being exposed to the liquid to be measured.

In a particular embodiment, the conductivity and temperature microsensors and the circuit board platform of the apparatus in accordance with the present invention are fabricated using reconfigurable lithography in combination with chemical etching and metallization or any standard PCB process. While other materials are within the scope of the present invention, Liquid Crystalline Polymer (LCP) was selected as the microsensor substrate due to its low moisture permeability properties, thus making it possible to withstand direct immersion in a harsh marine environment.

In an exemplary embodiment, once assembled, the dimensions of the entire CTD are 65 mm by 65 mm by 15 mm, and can be further compacted.

In an additional embodiment, the micro-CTD has RS 232 outputs, potentially allowing for real-time data acquisition, and is capable of being configured for placement on autonomous and remote underwater vehicles, living organisms or as stand-alone sensors.

The conductivity, temperature and pressure thin-film microsensors constitute a salinity total analysis system with integrated open path fluidics and electronic functionality fabricated in an economical format. A commercial analog-to-digital converter combined with a microcontroller and flash memory forms a microprocessor for the CTD system, allowing for easy data acquisition.

As such, the micro-CTD in accordance with the present invention provides a low cost system that is potentially expendable and allows cost effective networks of the system to be built. In addition, the micro-CTD of the present invention is substantially smaller than other CTDs known in the art and can therefore be embedded in novel configurations that are better suited to the user.

The advantages of the apparatus of the present invention over other CTDs known in the art include: (1) a combination of flexible, rigid and semi-rigid components in a flat, planar design allows the CTD to be used in numerous applications, (2) the low cost of the device allows for cost effective solutions, and (3) the embedded wireless capability allows for remote administration. Other advantages will become apparent upon review of the detailed description of the invention.

BRIEF DESCRIPTION OF THE DRAWINGS

For a fuller understanding of the invention, reference should be made to the following detailed description, taken in connection with the accompanying drawings, in which:

FIG. 5 is a diagram illustrating the PCBMEMS fabrication process flow using LCP as a substrate in accordance with the present invention;

DETAILED DESCRIPTION OF THE PREFERRED EMBODIMENT

The conductivity, temperature and pressure measurement instrument in accordance with the present invention includes three microsensors: (1) a conductivity cell (2) a resistive temperature device and (3) a pressure sensor. The three microsensors are fabricated and integrated into a small form factor on a printed circuit board. In a specific embodiment the conductivity cell and temperature device are designed and fabricated using LCP material and PCBMEMS techniques. The pressure sensor is a piezoresistive pressure sensor that is integrated within the circuit board of the system.

Figure 1A:
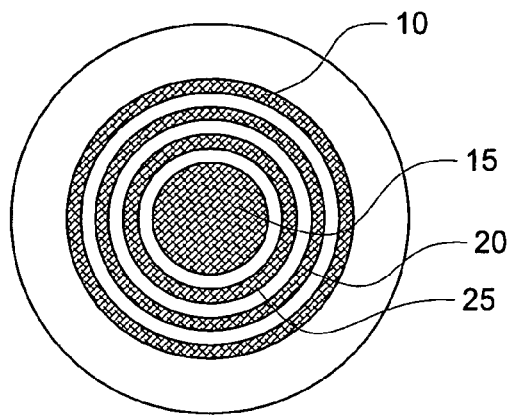
FIG. 1 is an illustrative set of photos illustrating the planar thin-film conductivity cell and the connection fingers on the backside of the conductivity cell in accordance with the present invention.
Figure 1B:
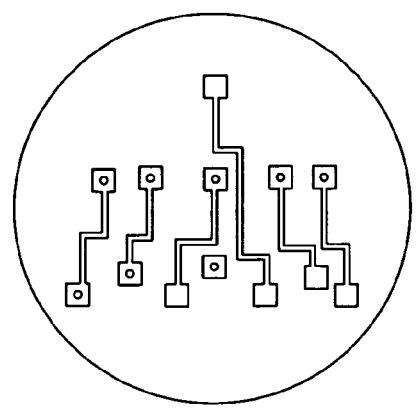

With reference to FIG. 1, the electrode configuration of the conductivity cell in accordance with the present invention is illustrated in which FIG. 1(A) illustrates the top-side of the planar thin-film conductivity cell having two drive electrodes 10 and 15 and two sense electrodes 20 and 25 in an annular, concentric configuration. FIG. 1(B) illustrates the connecting fingers on the backside of the conductivity cell. The design of the conductivity cell is motivated by several objectives, including: (1) small size (2) corrosion resistant (3) biofouling resistant (4) high accuracy (5) high stability. To meet these objectives, in a particular embodiment, the conductivity cell is a planar thin-film, four-electrode, conductivity cell fabricated of electroless nickel/gold/platinum black metals on 8-mil thick LCP material. In a specific embodiment, the conductivity cell, with connecting fingers, is approximately 11 mm by 11 mm in size. The cell is of planar and circular geometry such that all the current between the innermost 15 and outermost 10 ring drive electrodes passes through the two middle ring sense electrodes 20 and 25.

Figure 2:
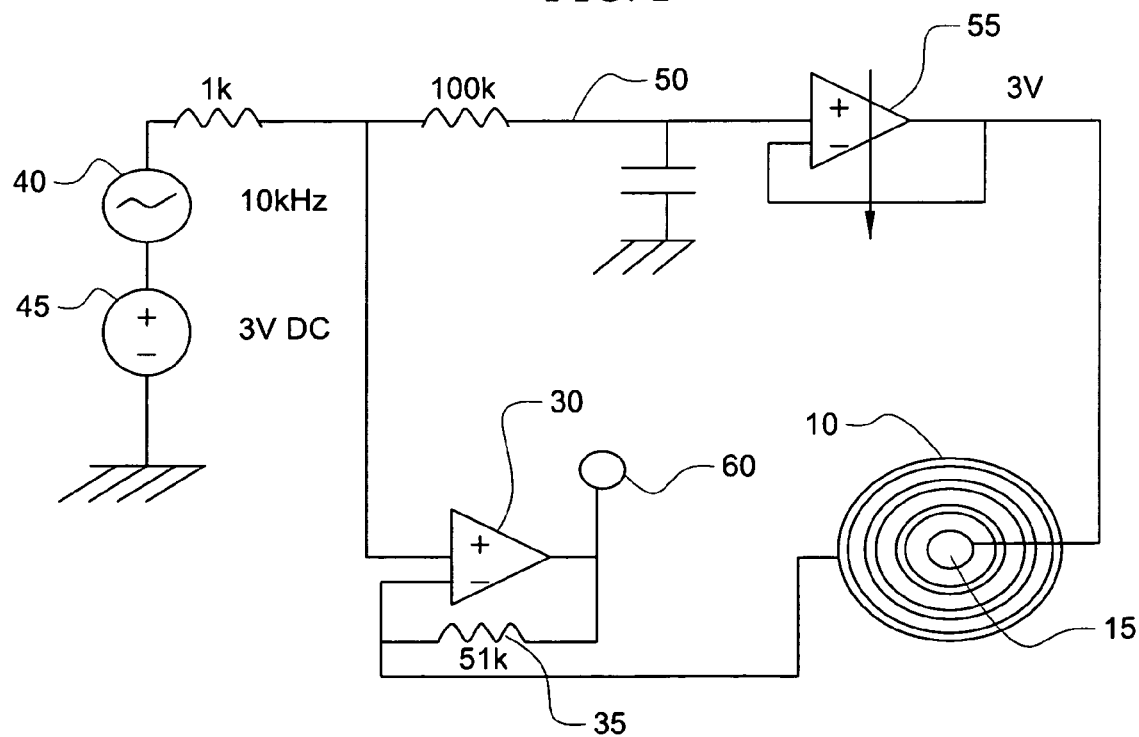
FIG. 2 is a schematic illustrating the circuitry of the conductivity circuit in accordance with the present invention.

Four-electrode conductivity cells are known in the art having an annular concentric configuration. With reference to FIG. 2, a schematic illustrating the supply circuitry and output circuitry for the conductivity microsensor is provided. To determine the conductivity of the cell, the voltage developed between the two points 10 and 15 and the area between those electrodes needs to be measured. According to the present invention these measurements are predetermined by the fabrication positioning of the electrode rings. By maintaining an 800 mV peak to peak (pkpk) between the outer 10 and inner 15 electrodes supplied by an operation amplifier 30 with a 51 ohm resistor 35, the current can be calculated using the formula V=IR and the area between the electrodes is known. The four electrode design is desirable because a differential amplifier between the two intermediate electrodes can be used to calculate the conductivity since those electrodes will not corrode due to the lack of current (a few picoamps) passing between them. The drive signal is then used to verify the extent of sensor corrosion because the distance between the drive and sense electrodes is fixed by the geometry and only biofouling can change their shape, contact and area. The voltage and resistive values are exemplary and other values are within the scope of the present invention.

In an exemplary embodiment, to measure the conductivity of the cell, a 10 kHz sine wave 40 across the outer 10 and inner 15 electrodes is employed. It was determined through testing that no more than 800 mV between the two electrodes could be used without causing electrolysis and metal corrosion. Due to the capacitive nature of the cell, the potential between the two electrodes undergoes a doubling action as the signal swings from one polarity to the next and thus the amplitude chosen was 400 mV. It is preferred to keep the device in a single supply configuration and thus a 3V DC bias 45 was added to the signal. To compensate for the 3V offset, the signal is filtered by a low pass filter 50 with a large time constant and then fed to an op-amp follower circuit 55 whose output is applied to the inner electrode 15. To maintain the maximum resolution, retain linearity in conductivity measurement, and to limit the number of measurement points, the signal is fed to the non-inverting input of the op-amp 55 and using a 51 ohm negative feedback resistor 35, attached the outer ring 10 of the cell to the inverting input of the op-amp 30. This op-amp circuit maintains the 800 mV pkpk signal on the outer ring 10 despite changes in conductivity in the cell. To make the current measurement, the pkpk voltage at the output of the op-amp 60 is measured.

Figure 3:
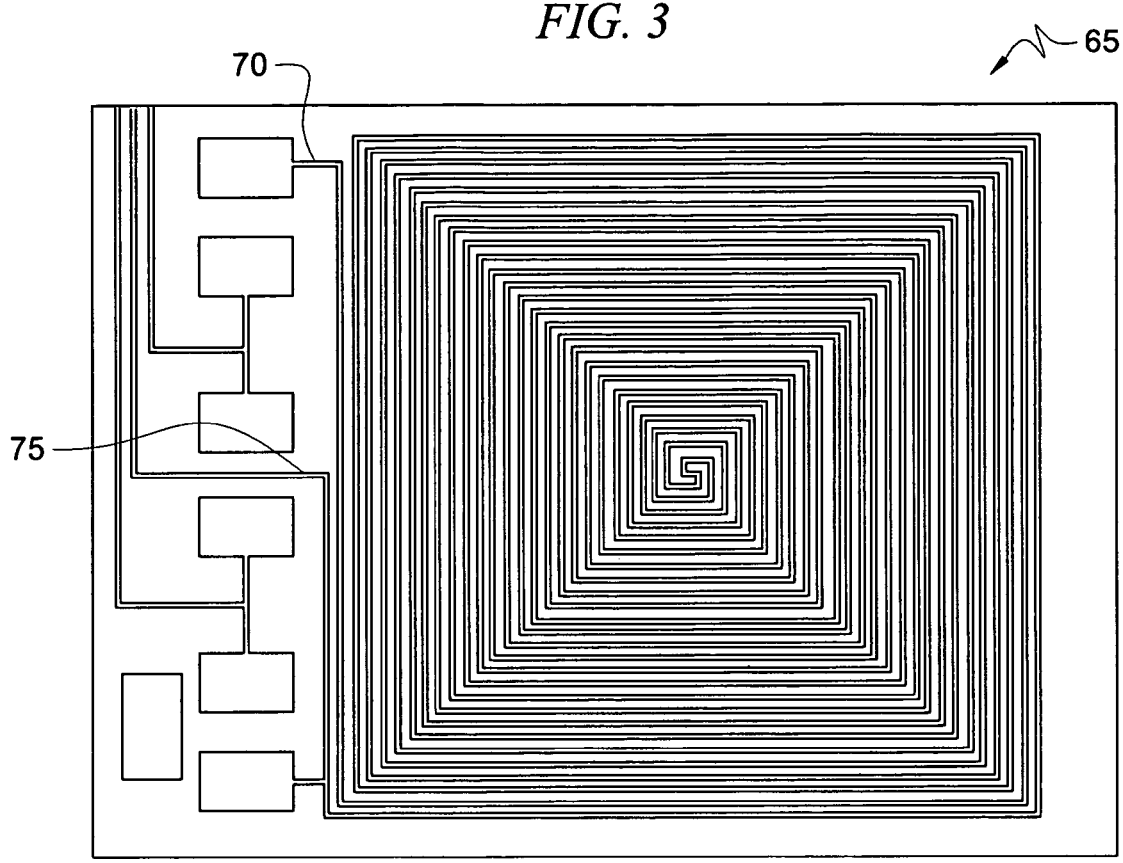
FIG. 3 is a photo illustrating the resistive temperature device (RTD) microfabricated on copper-clad LCP material in accordance with the present invention.

As shown the reference to FIG. 3, the resistive temperature device (RTD) 65 in accordance with the present invention is a thin film metallic circuit that exhibits a linear change in resistance with a change in temperature. By using the formula $[r=r_0 (1+a (T-T_0)]$ the temperature can be calculated when the change in resistance is measured. The RTD designed for the CTD has a concentric design that consists of two parallel traces 70 and 75 with 90° angles that meet in the center. The 90° angles of the design reduce inductance (orthogonal fields), due to the side traces have varying lengths so that it does not resonate at a particular frequency. The side-by-side traces also reduce noise. The design is quite long in length to provide greater sensitivity. This design exhibits maximum packing density and enables the sensor to be flexible or rigid.

In a particular embodiment, the resistive temperature sensor is fabricated with copper-clad LCP material using PCB/MEMS microfabrication processes. Copper has been chosen as the base metal because it exhibits linear results over the desired temperature range (−5 to 50° C.), it limits bi-metal junctions and it is cost effective because it is pre-clad on the LCP material. After the device is fabricated the copper metal is plated with a thin layer of tin to reduce corrosion from oxidation. Additional metals are within the scope of the present invention for fabrication of the resistive temperature device.

Figure 4:
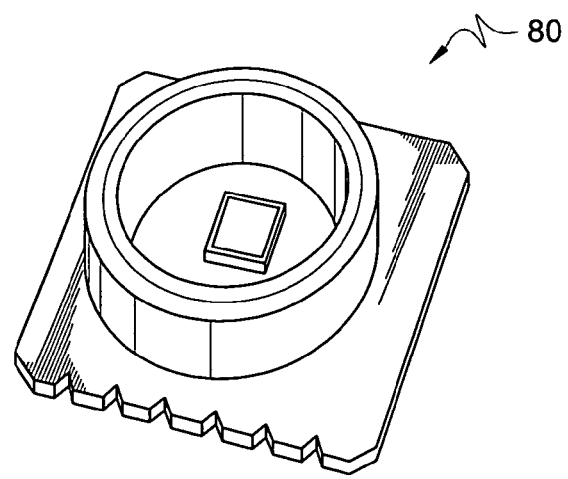
FIG. 4 is a photo illustrating the pressure sensor module in accordance with the present invention.

The pressure sensor used on the miniature CTD is a piezoresistive pressure sensor. In an exemplary embodiment, the piezoresistive pressure sensor is from Intersema (MS5535A). However, it is within the scope of the present invention to employ various pressure sensors in the micro-CTD. In particular one route to complete integration of the pressure sensing function is the incorporation of a multilayer electrode construction of LCP/Cu that would change it's dimension in proportion to the outside contact pressure. The features of the piezoresistive sensor in the exemplary embodiment include pressure range 0-14 bar (200 psi), 15 bit ADC, six coefficients stored on-chip for a software compensation, 3-wire serial interface, one system clock line (32.768 kHz), and low voltage/low power. With reference to FIG. 4, a photo of the pressure exemplary pressure sensor module (Intersema MSS53SA) is provided.

In a specific embodiment, the conductivity cells of the present invention are fabricated using PCB/MEMS processes and techniques except for the finishing metal applied. A variety of metal configurations are within the scope of the present invention, including, but not limited to: 1) electroless nickel with electroless gold 2) electroless nickel with electrolytic gold 3) electroless nickel, electrolytic gold and platinum black.

With reference to FIG. 5, in a particular embodiment, the electrode patterns are exposed onto the LCP material by using a maskless reconfigurable photoimaging tool (SF-100) and a negative photoresist (Dupont 950). After the pattern has been developed (NaCO$_3$) and is visible, the holes (10 mil) are drilled in the LCP material. Then the LCP is catalyzed and plated for 2 minutes with electroless nickel solution (Enthone 425). After nickel deposition, the electrode pattern is aligned to the plated through holes and re-exposed using the SF-100 process. Once the pattern is developed, the excess nickel is chemically etched away using an aqueous aqua regia solution. Then the conductivity cell is plated with electroless nickel solution for 2 hours to acquire a thickness of 1 mil (0.001 inches). Upon completion of the nickel-plating, either electroless gold (Transene) or electrolytic gold (Technic) is applied. The third electrode metal configuration involves depositing a platinum black solution (YSI) to the electrolytic gold to increase the surface area of the conductivity cell. A diagram of the exemplary PCBMEMS process flow using LCP as substrate is illustrated with reference to FIG. 5. The resistive temperature device is fabricated using the same photoimaging tool (SF100) to expose the pattern on the copper-clad LCP substrate. In this case a positive photoresist is used. After the pattern is developed the excess copper is etched away using a sodium persulfate solution. Then a thin tin metal coating is applied to prevent corrosion from oxidation.

Figure 6B:
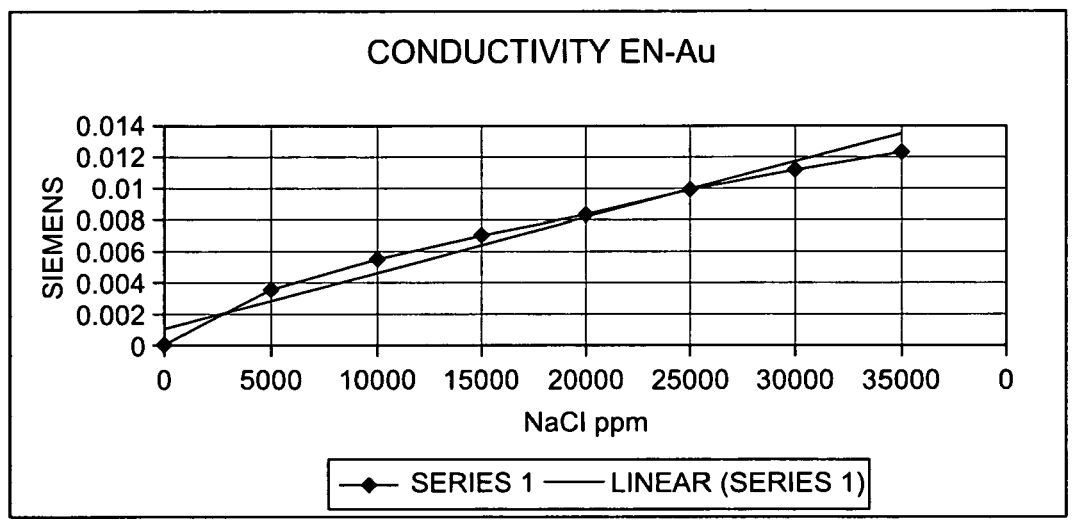
FIG. 6 is a set of graphs illustrating the three metal configurations for the conductivity cell (EN-Eau, EN-Au, EN-Au—Pt) plotting NaCl ppm vs. Siemens.
Figure 6C:
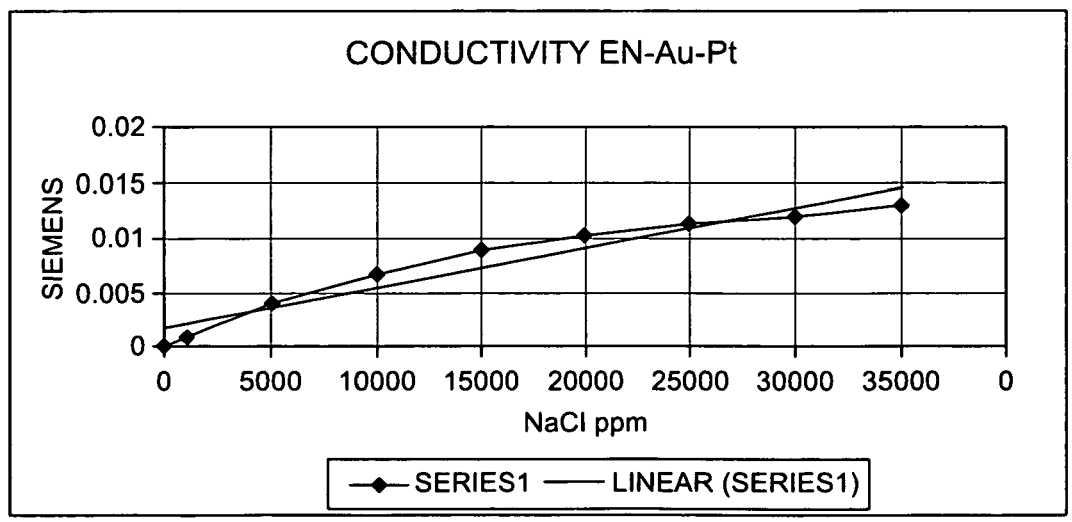

With reference to FIG. 6, experimental measurements of the conductivity cells have been tested in the laboratory using sodium chloride concentrations ranging from 0 to 35,000 ppm. The conductivity cells were electrically connected to the test circuits, a function generator and an oscilloscope. The function generator maintains the 10 kHz sine wave across the inner and the outer electrodes and the oscilloscope measures the pkpk voltages after 40 averages. The conductivity (siemens) was then calculated using the conductance formula where $C=I/V$ and then plotted against the sodium chloride concentrations (ppm) for the three different metal configurations. The results of the combination of electroless nickel/electroless gold are shown in FIG. 6(A). The results of the combination of electroless nickel/gold are shown with reference to FIG. 6(B). The results of electroless nickel/gold/platinum black are shown with reference to FIG. 6(C).

Figure 7A:
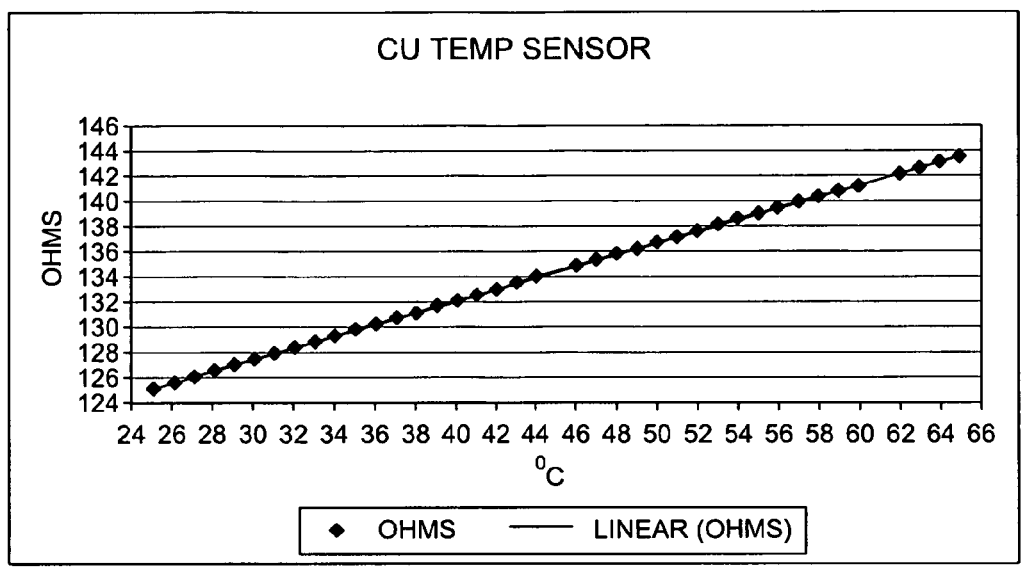
FIG. 7 is a set of graphs illustrating the copper-clad LCP RTD in Temperature vs. ohms.
Figure 7B:
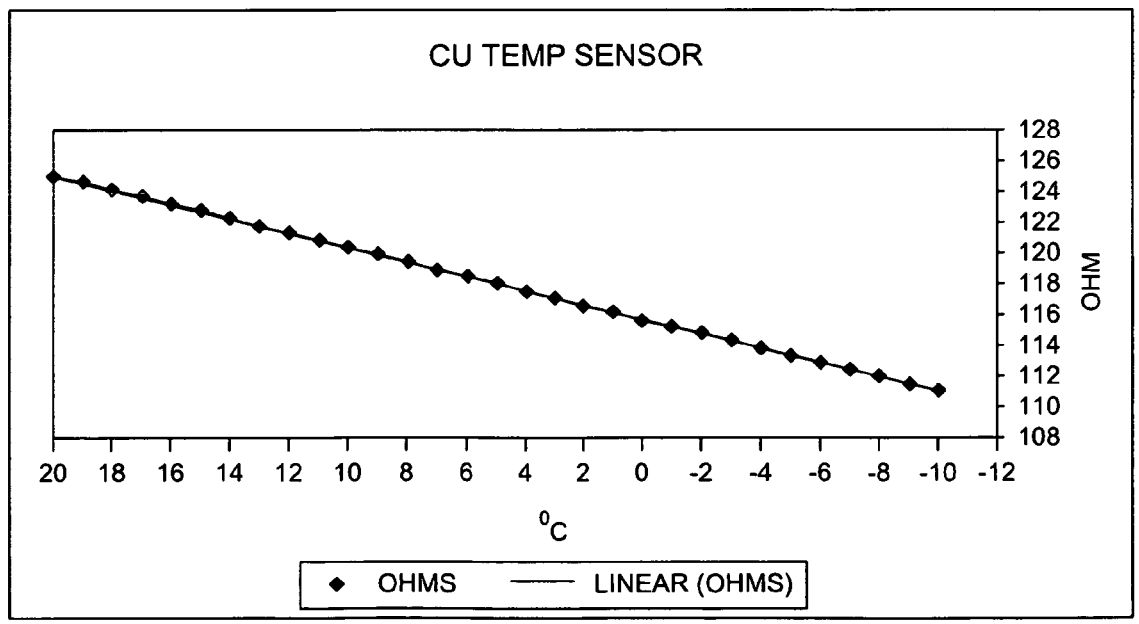

Experimental testing of the copper-clad LCP CTD has been carried out in the laboratory using a Thermotron temperature test chamber that produced a temperature range from 12 to 65° C. A thermocouple and a multimeter were connected to the sensor and then it was placed inside the temperature test chamber. The temperature and ohm readings were recorded and plotted. The results are shown in FIG. 7(A) and FIG. 7(B) for two different temperature ranges.

In a particular embodiment, the CTD system will be packaged so that the three sensors are mounted on the surface of the housing exposed to the environment in a planar design.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An apparatus for measuring conductivity, temperature and depth of a liquid, the apparatus comprising:
   a substantially planar thin-film conductivity microsensor integrally fabricated on a liquid crystalline polymer substrate, the conductivity microsensor for measuring the conductivity of the liquid;
   a substantially planar thin-film resistive temperature microsensor integrally fabricated on a liquid the liquid crystalline polymer substrate, the conductivity microsensor for measuring the temperature of the liquid; and
   a discrete pressure microsensor mounted on the liquid crystalline polymer substrate for measuring the pressure of the liquid.

2. The apparatus of claim 1, wherein the conductivity microsensor further comprises a four electrode conductivity sensor further comprising four concentric annular electrodes fixed in relative position to each other.

3. The apparatus of claim 2, wherein the four concentric annular electrodes are fabricated of electroless nickel and electrolytic gold.

4. The apparatus of claim 2, wherein the four concentric annular electrodes are fabricated of electroless nickel, electrolytic gold and platinum black.

5. The apparatus of claim 2, wherein the four concentric annular electrodes are fabricated of electroless nickel and electroless gold.

6. The apparatus of claim 1, wherein the conductivity microsensor further comprises supply circuitry coupled to the four concentric annular electrodes and output circuitry coupled to the four concentric annular electrodes for measuring the conductivity of the liquid.

7. The apparatus of claim 1, wherein the substantially planar thin-film resistive temperature microsensor further comprises a thin-film metallic circuit exhibiting a linear change in resistance with a change in the temperature of the liquid.

8. The apparatus of claim 1, wherein the substantially planar thin-film resistive temperature microsensor further comprises two parallel metallic traces having 90° angles and meeting at a center point.

9. The apparatus of claim 1, wherein the discrete pressure microsensor is a piezoresistive pressure sensor.

10. The apparatus of claim 1, wherein the discrete pressure microsensor is a multilayer electrode of LCP/Cu construction adapted to change its dimension in proportion to the contact pressure of the liquid.

11. The apparatus of claim 1, further comprising a data-acquisition and processing system connected to receive measurement signals from the conductivity microsensor, the temperature microsensor and the pressure microsensor.

12. The apparatus of claim 1, further comprising embedded wireless functionality connected to transmit measurement signals from the conductivity microsensor, the temperature microsensor and the pressure microsensor.

13. The apparatus of claim 1, further comprising a substantially watertight casing to protect the apparatus from exposure to the liquid.

* * * * *